US012806009B2

(12) United States Patent
Lo

(10) Patent No.: US 12,806,009 B2
(45) Date of Patent: Nov. 24, 2026

(54) REPLACEMENT HEART VALVE

(71) Applicant: Medical Equipment Design Innovation, Inc., Irvine, CA (US)

(72) Inventor: Pham Cong Lo, Rancho Mission Viejo, CA (US)

(73) Assignee: Medical Equipment Design Innovation, Inc., Irvine, CA (US)

( * ) Notice: Subject to any disclaimer, the term of this patent is extended or adjusted under 35 U.S.C. 154(b) by 538 days.

(21) Appl. No.: 18/371,351

(22) Filed: Sep. 21, 2023

(65) Prior Publication Data

US 2025/0099236 A1 Mar. 27, 2025

(51) Int. Cl.
*A61F 2/24* (2006.01)

(52) U.S. Cl.
CPC .......... *A61F 2/2418* (2013.01); *A61F 2/2433* (2013.01); *A61F 2220/0016* (2013.01)

(58) Field of Classification Search
CPC ........ A61F 2/24; A61F 2/2412; A61F 2/2415; A61F 2/2442; A61F 2/2445; A61F 2/2457; A61F 2/2409; A61F 2/2418; A61F 2/2427; A61F 2/2433; A61F 2250/0069; A61F 2/243; A61F 2/246; A61F 2/86; A61F 2/89; A61F 2/90; A61F 2250/006; A61F 2250/0063; A61F 2220/0025
See application file for complete search history.

(56) References Cited

U.S. PATENT DOCUMENTS 8,021,420 B2 9/2011 Dolan
10,531,872 B2 * 1/2020 Hacohen ............... A61F 2/2418
2014/0324164 A1 * 10/2014 Gross .................... A61F 2/2418 623/2.37
2020/0000579 A1 1/2020 Manash et al.
2020/0038180 A1 * 2/2020 Oba ...................... A61F 2/2418
2020/0222180 A1 7/2020 Lane et al.
2020/0337838 A1 10/2020 Ratz et al.
2022/0192823 A1 * 6/2022 Darekar ................ A61F 2/2418
2022/0249228 A1 8/2022 Vidlund et al.
2023/0190462 A1 6/2023 Nir et al.
2025/0099236 A1 * 3/2025 Lo ......................... A61F 2/2436

FOREIGN PATENT DOCUMENTS

WO WO-2014144937 A2 * 9/2014 ........... A61F 2/2418
WO WO2020/210652 A1 10/2020

OTHER PUBLICATIONS

International Search Report and Written Opinion dated Jan. 30, 2025 for corresponding PCT Application No. PCT/US2024/046786.

* cited by examiner

*Primary Examiner* — Seema Mathew
(74) *Attorney, Agent, or Firm* — Raymond Sun

(57) ABSTRACT

A heart valve assembly has a skirt dish having a tissue skirt sutured to the skirt dish, and a valve support assembly having a leaflet assembly sutured to the valve support assembly. The skirt dish is connected to the valve support assembly. The valve frame and the annulus frame are made from different materials. A delivery system has a balloon catheter having a shaft, a balloon provided on the shaft adjacent the distal end of the catheter, and a valve frame seat located on the shaft directly proximal to the balloon. The delivery system also has a capsule that slidably covers the balloon and the valve frame seat in a manner such that the skirt dish is seated around the valve frame seat and the valve support is seated over the balloon.

14 Claims, 22 Drawing Sheets

REPLACEMENT HEART VALVE

BACKGROUND OF THE INVENTION

1. Field of the Invention

The present invention relates to prosthetic heart valves, and in particular, to a transcatheter mitral heart valve prosthesis that is adapted for replacing a native mitral valve.

2. Description of the Prior Art

Prosthetic heart valves have been used for many years to treat cardiac valvular disorders. The native heart valves (such as the aortic, pulmonary, and mitral valves) serve critical functions in assuring the forward flow of an adequate supply of blood through the cardiovascular system. These heart valves can be rendered less effective by congenital, inflammatory, or infectious conditions. Such conditions can eventually lead to serious cardiovascular compromise or death. For many years the definitive treatment for such disorders was the surgical repair or replacement of the valve during open heart surgery, but such surgeries are dangerous and prone to complication.

More recently a transcatheter technique has been developed for introducing and implanting a prosthetic heart valve using a flexible catheter in a manner that is less invasive than open heart surgery. In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve, such as by inflating a balloon on which the valve is mounted. Alternatively, the valve can have a resilient, self-expanding stent or frame that expands the valve to its functional size when it is advanced from a delivery sheath at the distal end of the catheter.

Unlike the aortic valve, however, the mitral valve annulus does not provide a good landmark for positioning a replacement mitral valve. In patients needing a replacement aortic valve, the height and width of the aortic annulus are generally increased in the presence of degenerative disease associated with calcium formation. These changes in tissue make it easier to properly secure a replacement aortic valve in place due to the reduced cross-sectional area of the aortic annulus. The degenerative changes typically found in aortic valves are not, however, present in mitral valves experiencing regurgitation, and a mitral valve annulus is therefore generally thinner than the annulus of a diseased aortic valve. The thinner mitral valve annulus makes it relatively more difficult to properly seat a replacement mitral valve in the native mitral valve annulus. The general anatomy of the mitral valve annulus also makes it more difficult to properly anchor a replacement mitral valve in place. The mitral valve annulus provides for a smoother transition from the left atrium to the left ventricle than the transition that the aortic valve annulus provides from the aorta to the left ventricle. The aortic annulus is anatomically more pronounced, providing a larger "bump" to which a replacement aortic valve can more easily be secured in place.

Thus, the larger mitral valve annulus makes it difficult to securely implant current percutaneously delivered valves in the native mitral position. Some attempts have been made to deliver and implant a one-piece replacement mitral valve, but it is difficult to provide a device that can be collapsed down to have a sufficiently small delivery profile and still be able to be expanded and secured in place within the mitral valve via a vascular access site.

In addition, the native mitral valve closes under high pressure. As a result, a replacement mitral valve needs to have a strong frame for solid anchoring in order to facilitate proper mitral valve function. Unfortunately, most of the known replacement mitral valve devices have a generally circular configuration with three leaflets, which is not optimal as the native mitral valve has two leaflets. When a native mitral valve opens, the pressure is about 25 mmHg, and when the mitral valve closes, the pressure is about 120 mmHg. However, a three-leaflet design needs a pressure of at least 90-100 mmHg for opening, and 140 mmgh for closing, which causes frame fatigue and adversely impacts the valve durability.

In addition, the supporting frame is usually made from Nitinol™, which is a very flexible material which makes it difficult to anchor the frame in the mitral annulus.

As a result, there remains a need for a replacement mitral valve device that has a valve support structure that can be securely and effectively positioned in the native mitral valve.

SUMMARY OF THE DISCLOSURE

It is an object of the present invention to provide a replacement mitral valve device that has a valve support structure that can be securely and effectively positioned in the native mitral valve.

To meet the objectives of the present invention, there is provided a mitral heart valve assembly having a skirt dish having a tissue skirt sutured to the skirt dish, and a valve support assembly having a leaflet assembly sutured to the valve support assembly. The leaflet assembly has a plurality of leaflets. The skirt dish is connected to the valve support assembly, and the skirt dish and valve support assembly are made from different materials.

The present invention also provides a delivery system having a balloon catheter having a shaft having a distal end, a balloon provided on the shaft adjacent the distal end, and a valve frame seat located on the shaft directly proximal to the balloon. A capsule is provided on the shaft of the balloon catheter and the capsule slidably covers the balloon and the valve frame seat. When the heart valve is crimped on the shaft of the balloon catheter for delivery, the skirt dish is seated around the valve frame seat, and the valve support assembly is seated over the balloon.

DETAILED DESCRIPTION OF THE PREFERRED EMBODIMENTS

Figure 1:
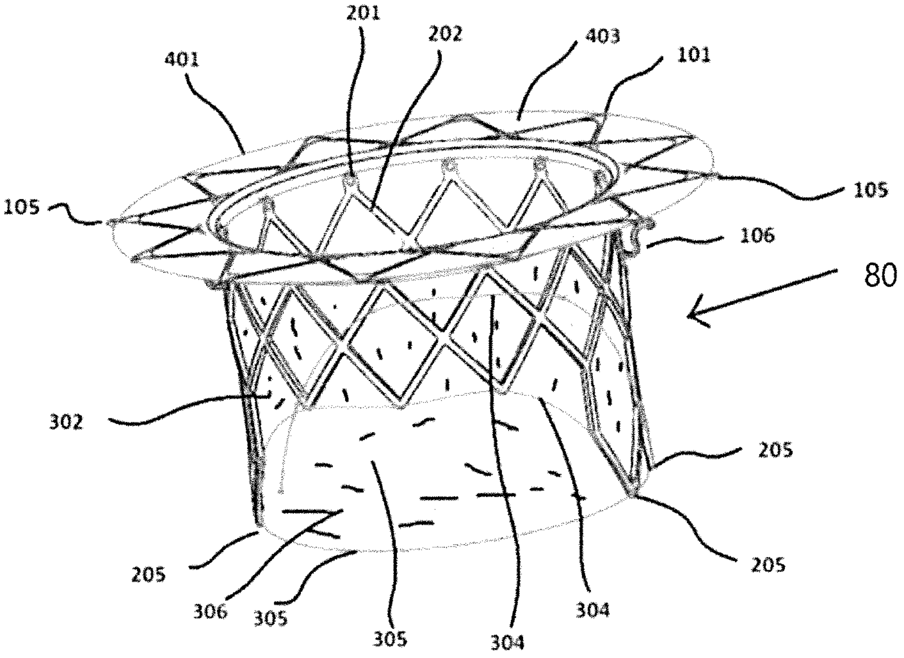
FIG. 1 is a perspective view of a mitral heart valve prosthesis according to one embodiment of the present invention shown before crimping on to a delivery device.
Figure 2:
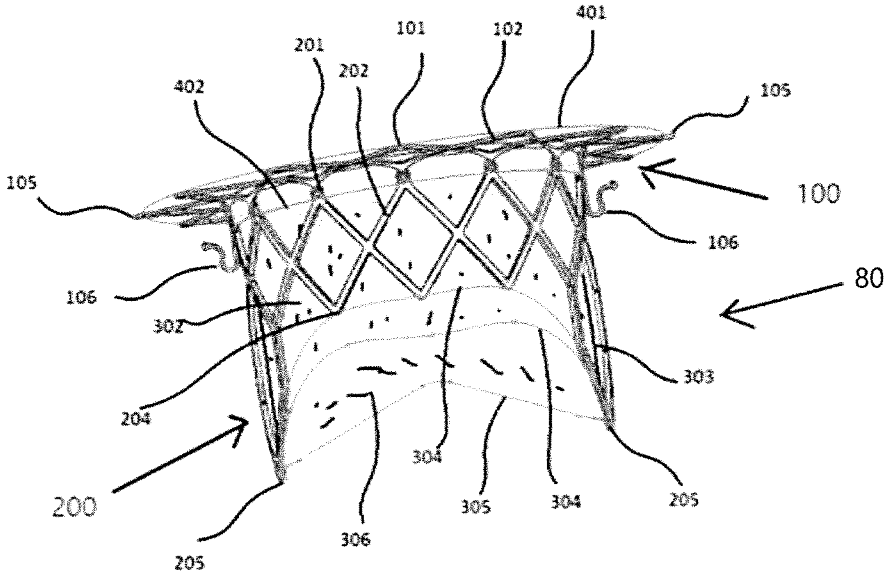
FIG. 2 is a side view of the heart valve prosthesis of FIG. 1.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides a transcatheter mitral heart valve prosthesis 80. Referring to FIGS. 1-20, the prosthesis 80 includes a skirt dish 100 and a valve support assembly 200. The valve support assembly 200 supports and retains a leaflet assembly 300, and a tissue skirt 400 that is secured to the skirt dish 100. The present invention essentially divides the overall frame of the prosthesis 80 into two separate frames that have two different types of materials that are adapted to provide more effective performance for their intended functions. Specifically, the valve support assembly 200 is provided in a more rigid material, such as cobalt chromium, so that it can better perform its intended function of securing the prosthesis 80 to the native annulus, while the skirt dish 100 is provided in a more flexible material, such as Nitinol™, so that it can better perform its intended function of supporting the leaflet assembly 300.

Figure 9:
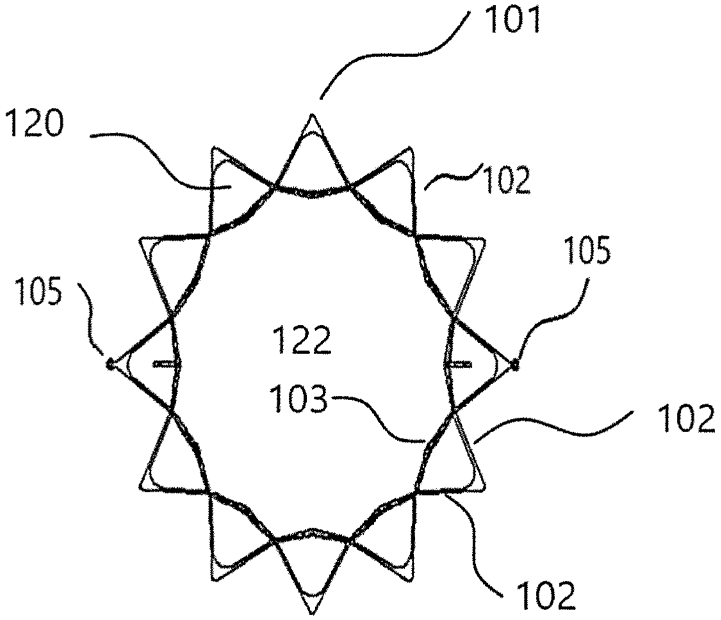
FIG. 9 is a top view of the frame of FIG. 8.
Figure 12:
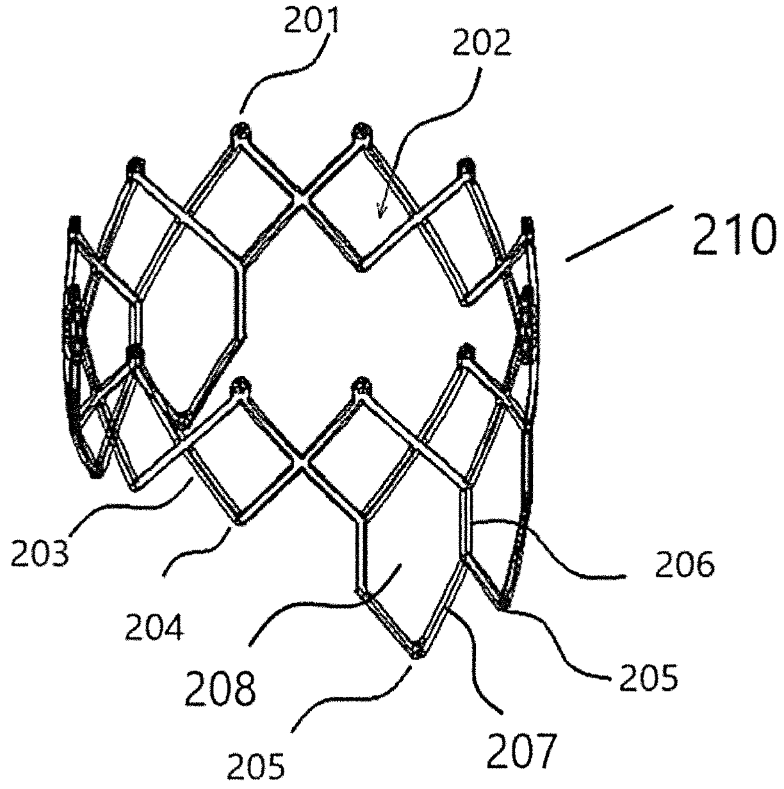
FIG. 12 is a top perspective view of the support skeleton of the valve support assembly of FIG. 6 shown before crimping on to a delivery device.
Figure 13A:
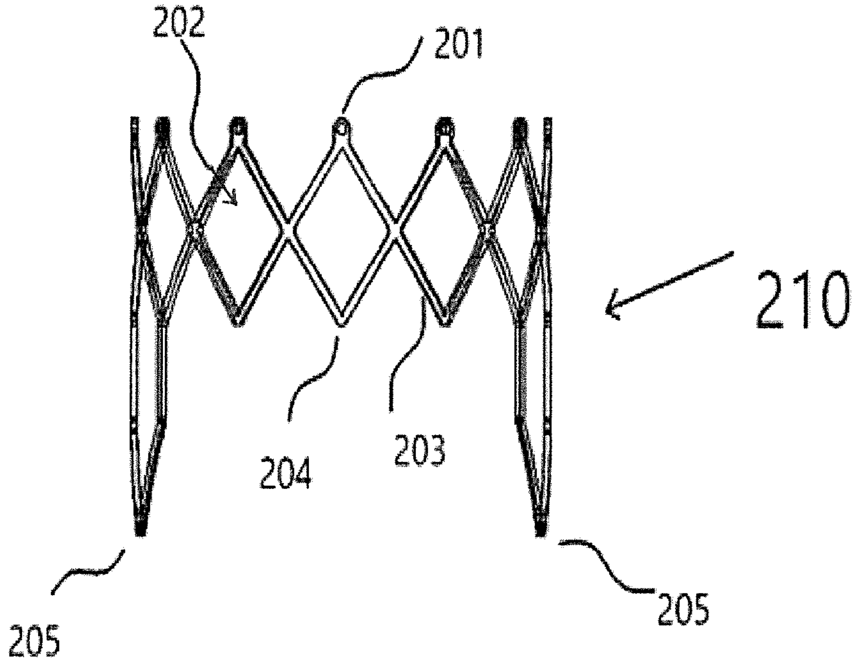
FIG. 13A is a side view of the support skeleton of FIG. 12.
Figure 13B:
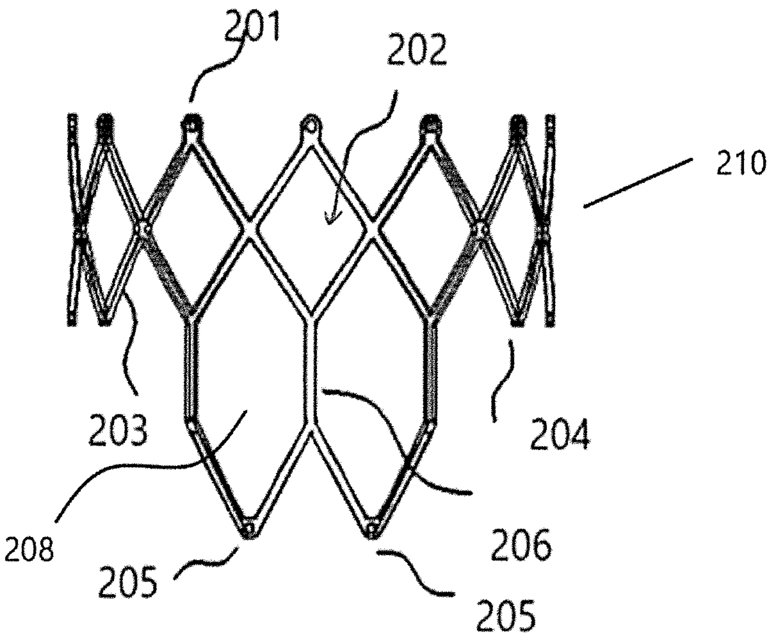
FIG. 13B is a side view of the support skeleton of FIG. 13A that has been turned by 90 degrees.
Figure 14:
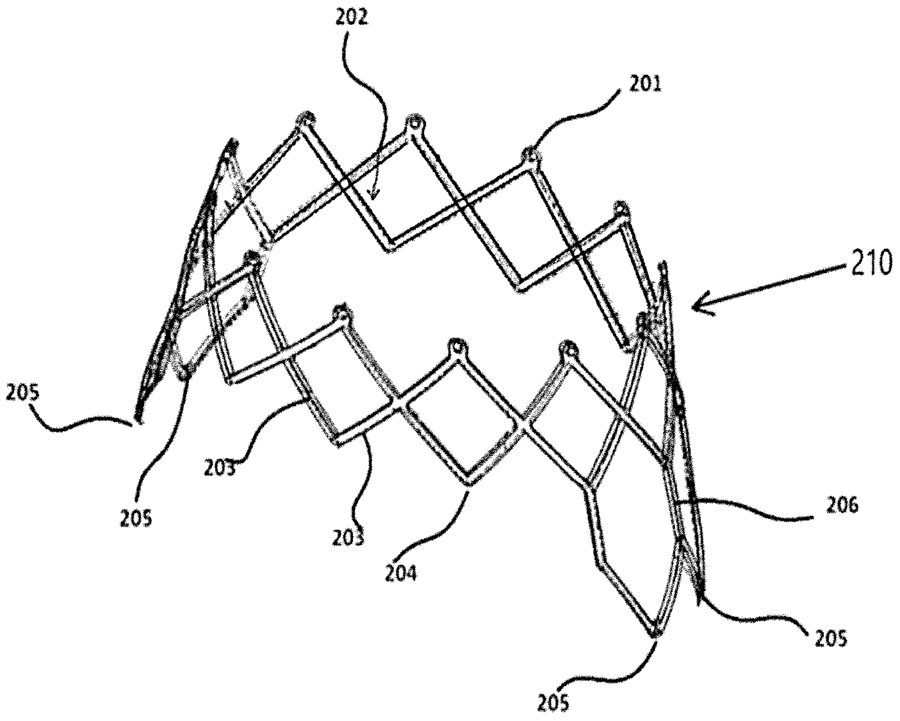
FIG. 14 is a top perspective view of the frame of FIG. 12 after expansion from the delivery device.

FIGS. 1-3, 15-16 and 20 show the entire prosthesis 80. FIGS. 4, 5, 8-11 and 17 show the skirt dish 100. FIGS. 6, 7, 12-14, 18 and 19 show the valve support assembly 200. FIGS. 9 and 12 show the leaflet assembly 300 and the annulus skirt 400, respectively.

In a human heart, blood flows from the left atrium through the mitral valve and towards the left ventricle. As used herein, the term "inflow side" shall mean the side of the prosthesis 80 from which blood from the left atrium enters, and the term "outflow side" shall mean the side of the prosthesis 80 where blood exits and flows towards the left ventricle. These flow directions are shown by arrows "Inflow" and "Outflow" in FIG. 3.

Starting with FIGS. 4, 5 and 8-11, the skirt dish 100 is preferably made from a less rigid and more flexible material, such as a self-expandable material such as Nitinol™. The skirt dish 100 has a generally circular configuration before crimping on to the delivery device, but assumes an oval configuration after self-expanding deployment in the human heart. The skirt dish 100 has a frame assembly that is comprised of twelve generally triangular cells 120, each of which can be identical to each other and configured so that the twelve cells 120 resemble petals surrounding the core of a flower. Each cell 120 is made up of two generally straight sides 102 connected at an apex 101, and with a concave side 103 connected to the two straight sides 102. The core in this case is an open central space 122 that is defined by the twelve concave sides 103.

Figure 10A:
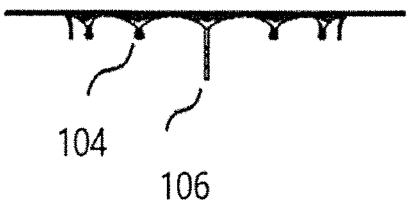
FIG. 10A is a side view of the frame of FIG. 8.
Figure 10B:
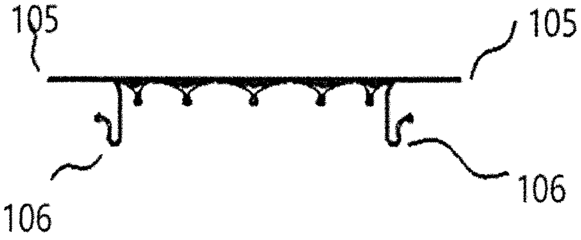
FIG. 10B is a side view of the frame of FIG. 10A that has been turned by 90 degrees.
Figure 11:
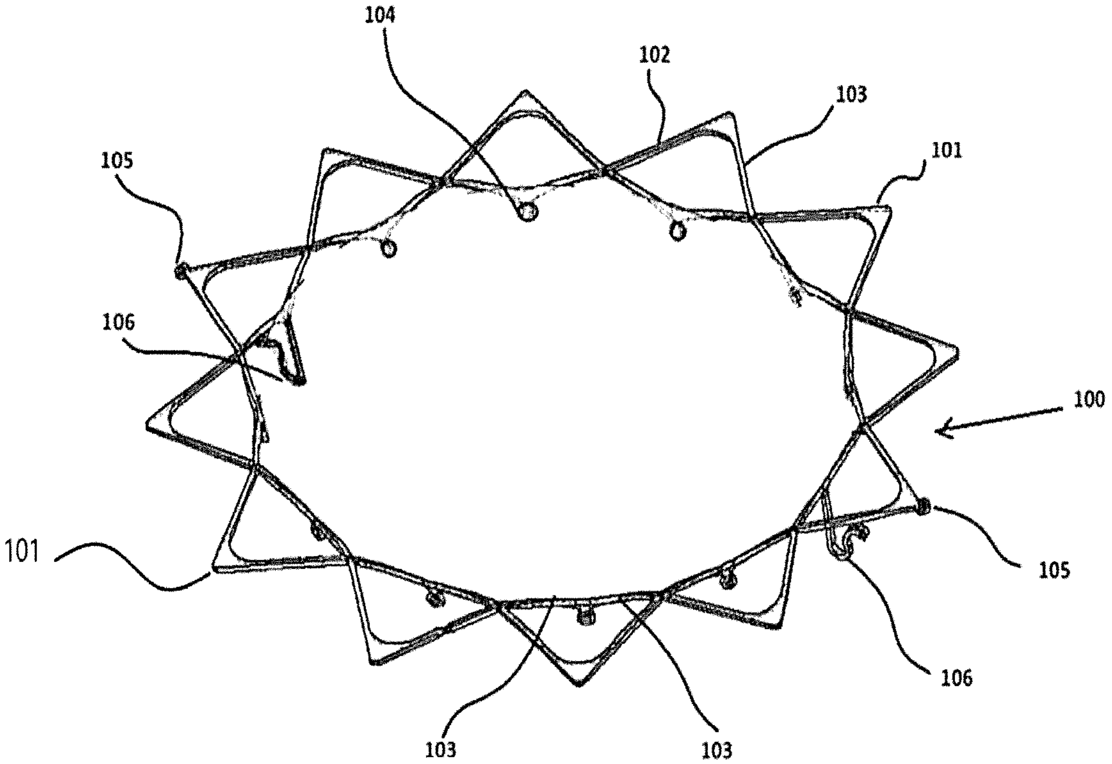
FIG. 11 is a top perspective view of the frame of FIG. 8 after expansion from the delivery device.

As best shown in FIGS. 10A and 10B, the cells 120 are all in the same general plane. Two hook-shaped anchors 106 extend vertically in the outflow direction from about the center of two opposing concave sides 103. An eyelet 105 is provided at the apex of the two cells 120 which have the anchors 106. A connector 104 extends vertically in the outflow direction from about the center of each of the other ten concave sides 103. Each connector 104 is shaped like an ear and the ten connectors 104 define a ring of connectors 104. A bump is provided at each connector 104.

Figure 4:
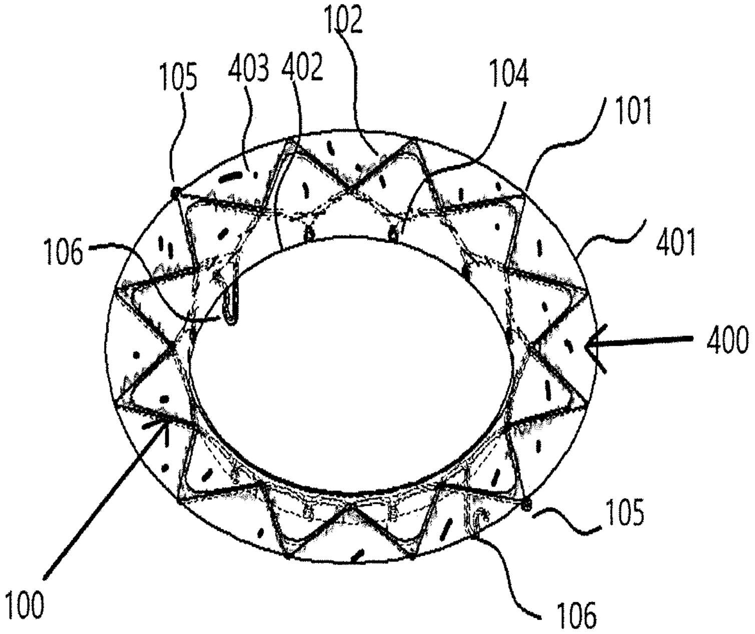
FIG. 4 is a top perspective view of the skirt dish of the heart valve prosthesis of FIG. 1 shown before crimping on to a delivery device.
Figure 5:
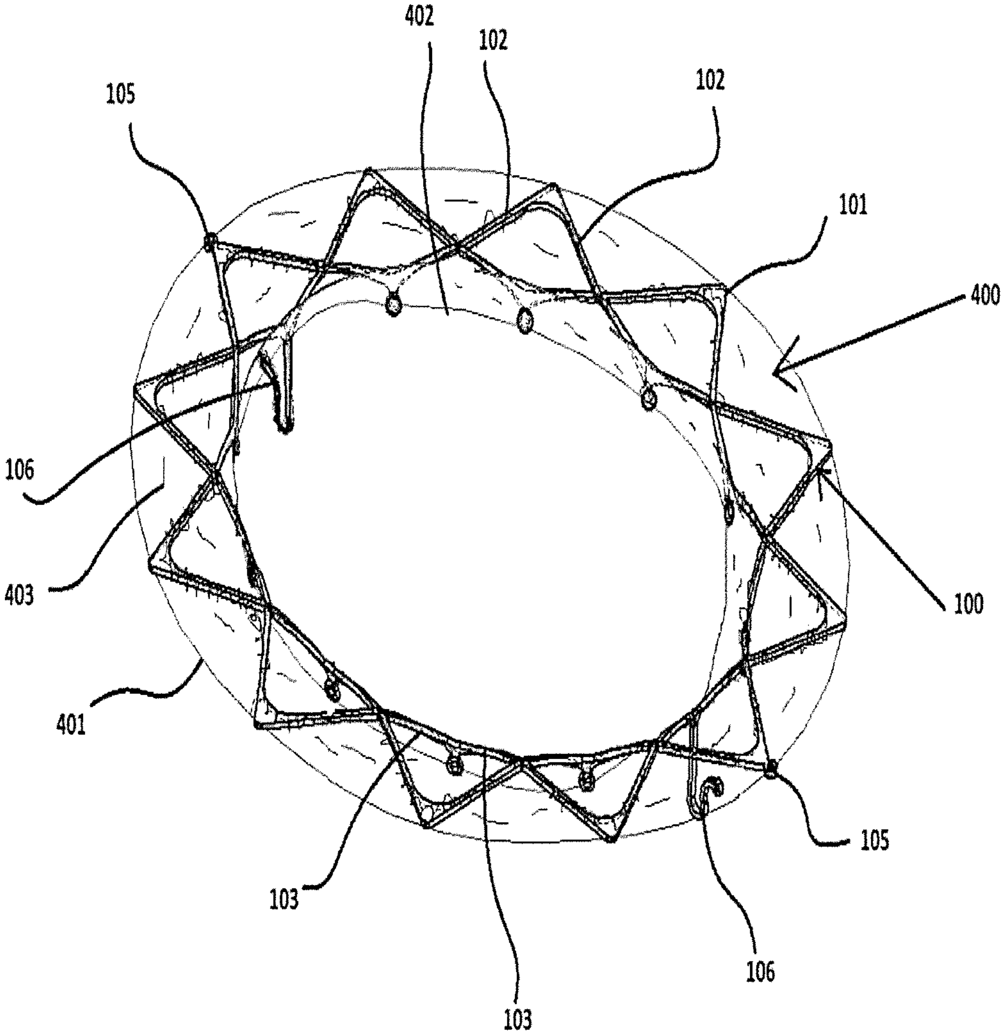
FIG. 5 is a top perspective view of the skirt dish of FIG. 4 after expansion from the delivery device.
Figure 17:
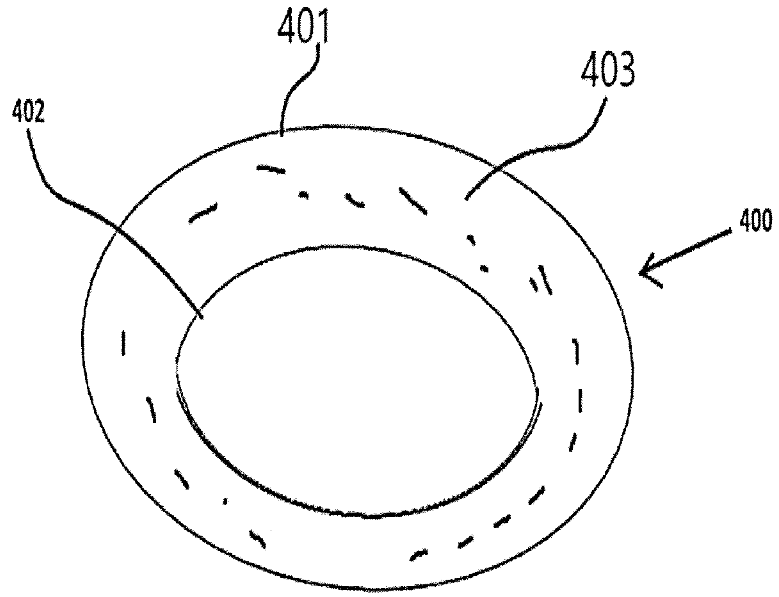
FIG. 17 is a top perspective view of the tissue skirt for the skirt dish of FIG. 4.

FIG. 17 illustrates the tissue skirt 400 that is secured to the frame assembly of the skirt dish 100. The tissue skirt 400 has a generally circular shape with a skirt portion 403 defined between an outer border 401 and an inner border 402. The inner border 402 is connected to the ring of connectors 104, and the skirt portion 403 is connected to the sides 102 and 103 of the cells 120, with the outer border 401 spanning the apices 101. The resulting skirt dish 100 is best shown in FIGS. 4 and 5, and the tissue skirt 400 has a concave configuration because the outer border 401 and the inner border 402 are positioned at different vertical levels, with the inner border 402 extending towards the outflow direction. FIG. 4 shows the skirt dish 100 before crimping on a delivery device, where the skirt dish 100 has a generally circular configuration, and FIG. 5 shows the skirt dish 100 after expansion and anchoring at a mitral annulus, where the skirt dish 100 has a generally oval and flared configuration.

Referring now to FIGS. 6, 7, 12-14, 18 and 19, the valve support assembly 200 has a support skeleton 210 which is preferably made from a more rigid material, such as cobalt chromium. The support skeleton 210 has a ring of cells 202.

Each cell 202 has four struts 203 that define a diamond-shaped configuration with an inflow apex 201 and an outflow apex 204. Each inflow apex 201 has an opening. Two commissure attachments are provided opposite to each other, and each commissure attachment has two hexagonal cells 208 extending in the outflow direction from the ring of cells 202. Specifically, each hexagonal cell 208 shares a strut 203 with two adjacent cells 202, and has two straight struts 206, each straight strut 206 extending from a separate apex 204, with two more struts 207 connecting at an outflow apex 205. Each pair of hexagonal cells 208 that make up a commissure attachment share one straight strut 206.

Figure 18:
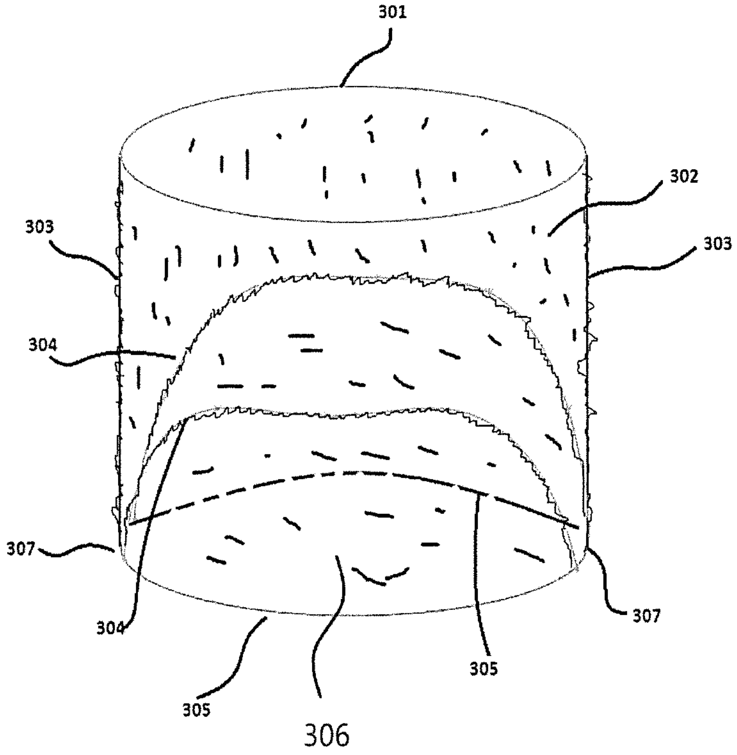
FIG. 18 is a top perspective view of the valve skirt and leaflets for the valve support assembly of FIG. 6.
Figure 19:
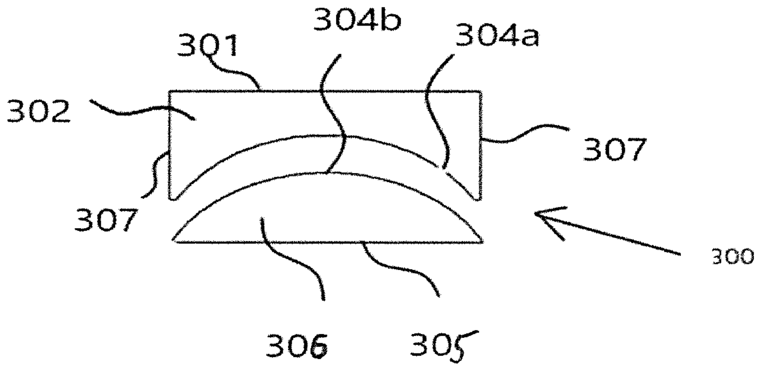
FIG. 19 is an exploded two-dimensional side view of the valve skirt and leaflets of FIG. 18.

The valve support assembly 200 also has a leaflet assembly 300, as best shown in FIGS. 18 and 19. The leaflet assembly 300 has a generally cylindrical tissue body 302 having an annular inflow edge 301 that is connected (e.g., by stitching) to the ring of inflow apices 201, and having a stitch line 303 that connects the tissue body 302 to the straight strut 206 that is shared by the two hexagonal cells 208 of each commissure attachment. An annular outflow edge 304A of the tissue body 302 is connected (e.g., by stitching) to the ring of outflow apices 204. Each of the two leaflets 306 has a free coaptation edge 305, and a skirt line 307 is connected to the straight strut 206 that is shared by the two hexagonal cells 208 of each commissure attachment to create a commissure for the valve. Each of the two leaflets 306 has an edge 304B that is adapted to be connected to the outflow edge 304A of the tissue body 302 along a stitch line 304. The valve support assembly 200 is adapted for two leaflets, therefore supporting a bi-leaflet heart valve.

Figure 6:
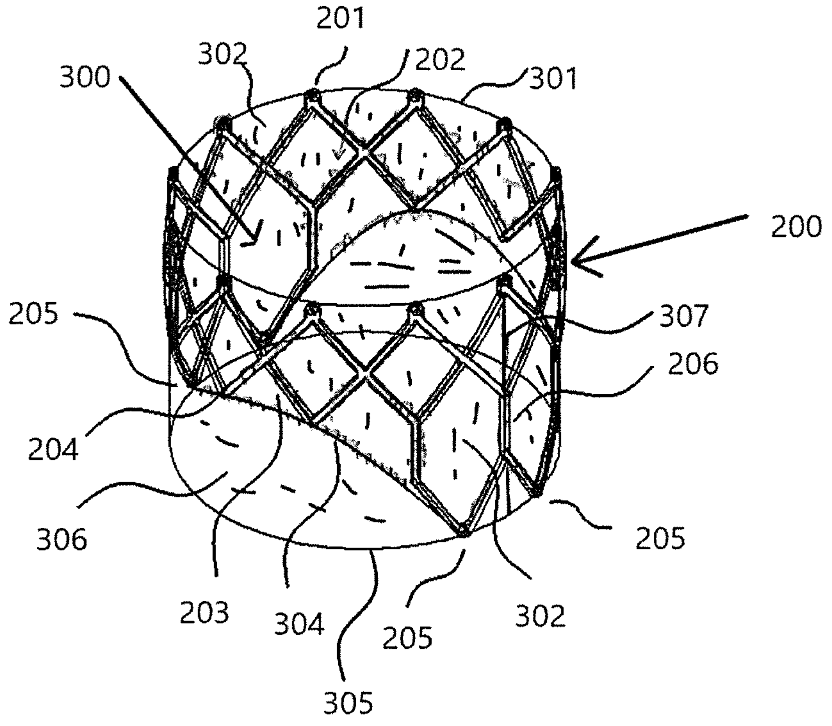
FIG. 6 is a top perspective view of the valve support assembly of the heart valve prosthesis of FIG. 1 shown with the valve open and before crimping on to a delivery device.
Figure 7:
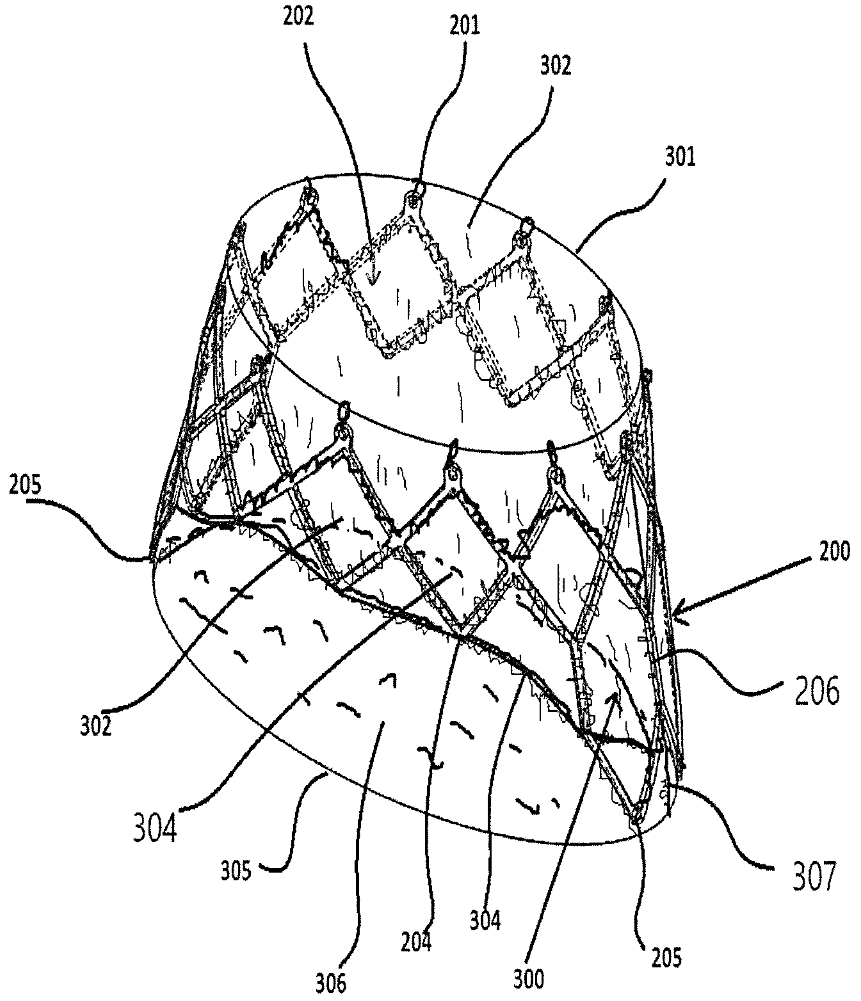
FIG. 7 is a top perspective view of the valve support assembly of FIG. 6 after expansion from the delivery device.
Figure 8:
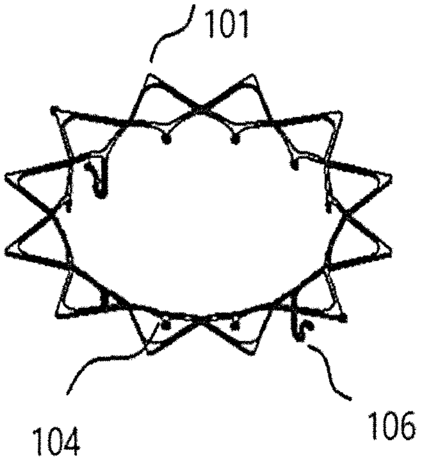
FIG. 8 is a top perspective view of the frame of the skirt dish of FIG. 4 shown before crimping on to a delivery device.

The resulting valve support assembly 200 is best shown in FIGS. 6 and 7. FIG. 6 shows the valve support assembly 200 before crimping on a delivery device, where the valve support assembly 200 has a generally circular configuration, and FIG. 7 shows the valve support assembly 200 after expansion and anchoring at a mitral annulus, where the valve support assembly 200 has a generally oval and flared configuration.

Figure 3:
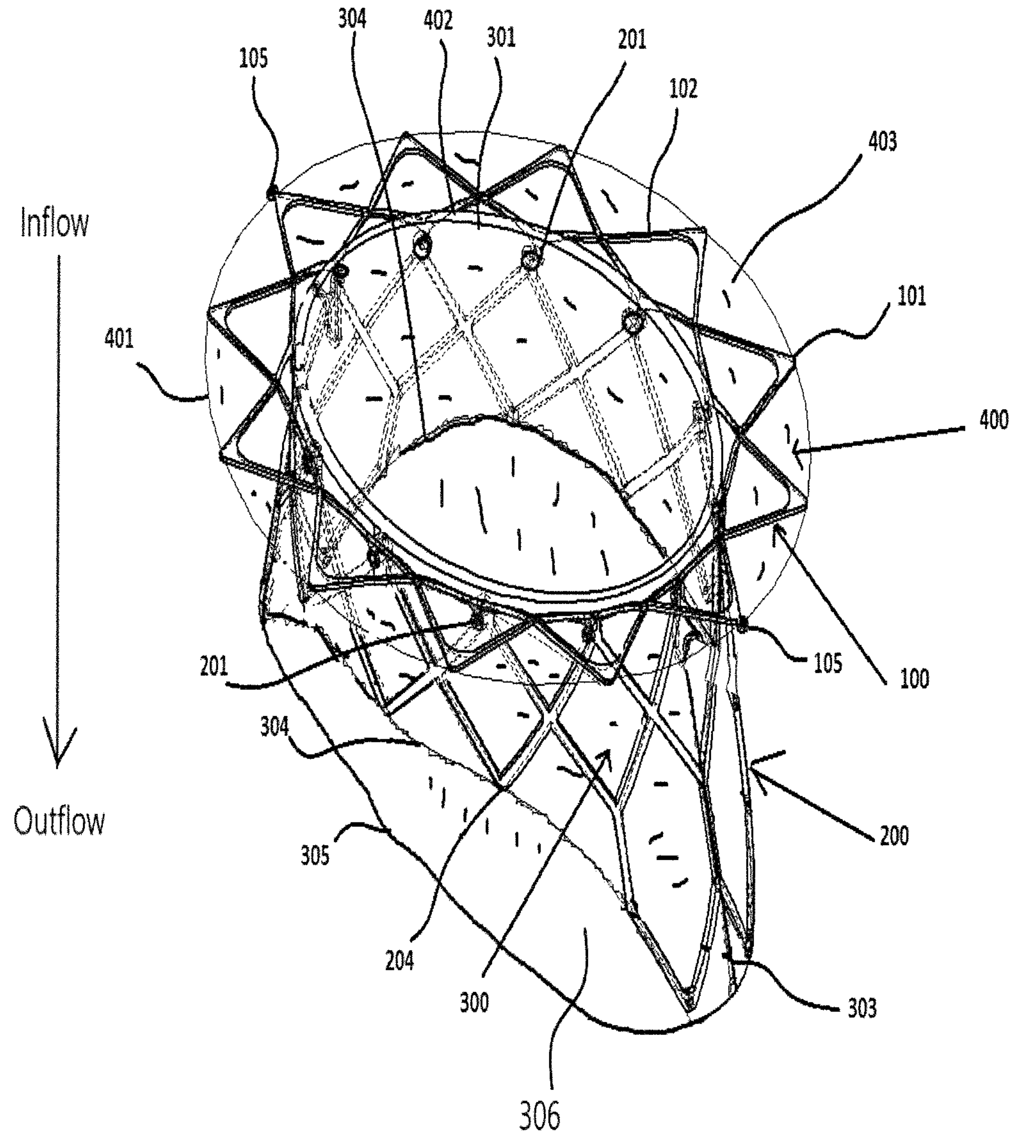
FIG. 3 is a top perspective view of the heart valve prosthesis of FIG. 1 after expansion from the delivery device.
Figure 20:
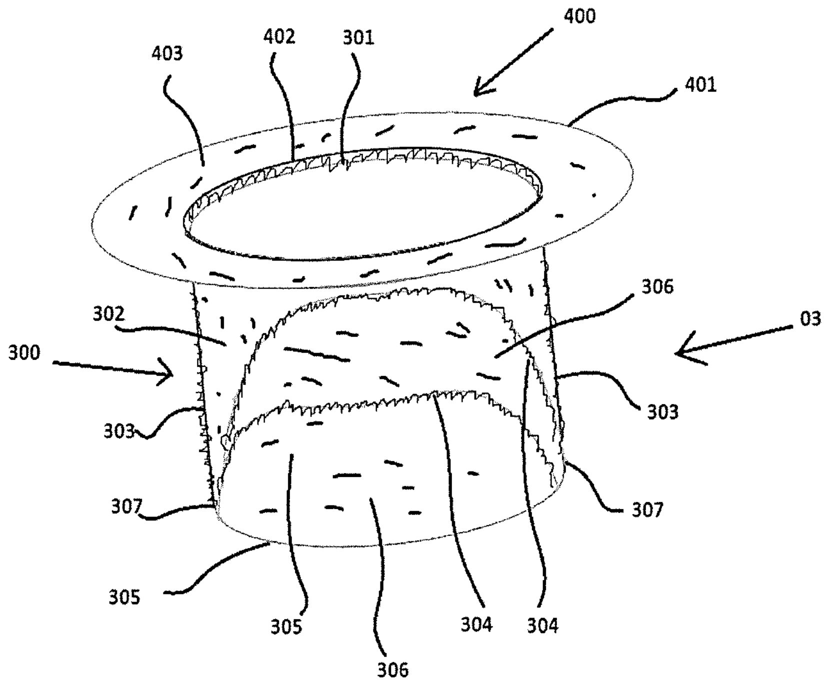
FIG. 20 is a top perspective view of the combined tissue skirt and skirt dish of FIG. 17 connected with the valve skirt and leaflets of FIG. 18.

FIG. 20 shows the prosthesis 80 before crimping on a delivery device, where the skirt dish 100 and the valve support assembly 200 have a generally circular configuration, and FIG. 3 shows the prosthesis 80 after expansion and anchoring at a mitral annulus, where the skirt dish 100 and valve support assembly 200 have a generally oval and flared configuration.

Figure 15:
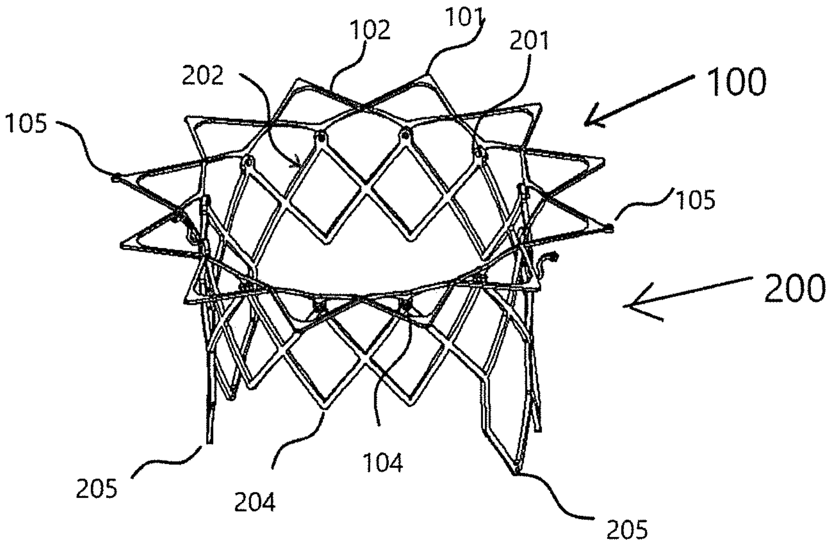
FIG. 15 is a top perspective view showing the frame of FIG. 8 connected to the support skeleton of FIG. 12.
Figure 16:
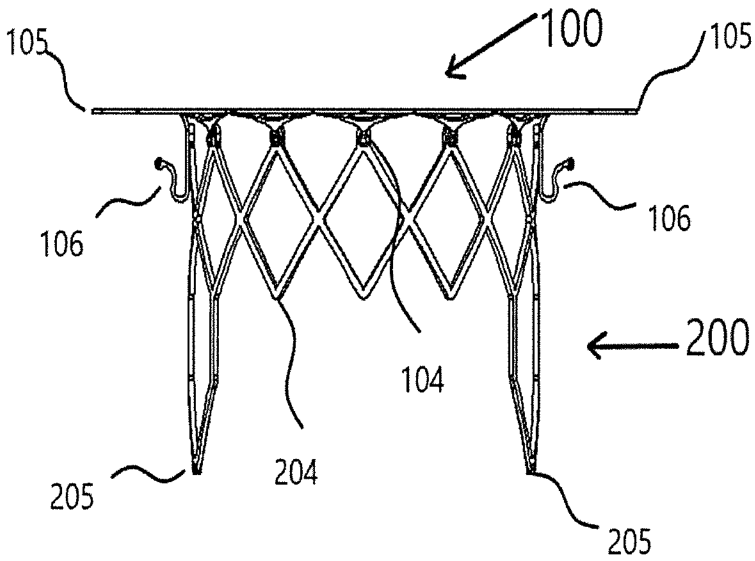
FIG. 16 is a side view of the combined frame and support skeleton of FIG. 15.

The combined skirt dish 100 and tissue skirt 400 is usually assembled separately from the combined valve support assembly 200 and leaflet assembly 300. The combined skirt dish 100 and tissue skirt 400 is then connected to the combined valve support assembly 200 and leaflet assembly 300. Referring to FIGS. 1-3 and 15-16, the inflow end of the combined valve support assembly 200 and leaflet assembly 300 is inserted into the interior of the outflow end of the combined skirt dish 100 and tissue skirt 400, and more specifically, inside the peripheral boundary defined by the anchors 106 so that the bumps in the connectors 104 are received inside openings of corresponding inflow apieces 201. This is best shown in FIGS. 15-16, and this engagement between the connectors 104 and inflow apices 201 secures the skirt dish 100 to the valve support assembly 200. In addition, the inner border 402 of the tissue skirt 400 is sutured to the inflow edge 301 of the leaflet assembly 300.

The skirt dish 100 is preferably made by nickel titanium small tubing (e.g., 7 mm). The design can be created by laser-cutting the tubing and can be shape-set with the desired profile. At under 5 degrees Celsius, the frame becomes elastic and is easy to load onto the balloon 602 at a small size. When the temperature reaches 37 degrees Celsius, the frame returns to its shape-set profile.

The valve support assembly 200 can be made by cobalt-chrome small tubing (e.g., 7 mm). The design can be laser-cut on the tubing and expanded like a shaped cylinder with a 23 mm, 26 mm, 29 mm, or 32 mm diameter.

FIGS. 21-25 illustrate a delivery system 700 that is adapted for use in delivering the prosthesis 80 to a mitral annulus, and deploying it at the mitral annulus. The delivery system 700 includes a balloon catheter and a capsule 703 that is sized and configured to ensheath and release the prosthesis 80.

The balloon catheter has a shaft 705 that extends from a T-junction (not shown) to a tapered distal tip 701. An inflatable balloon 702 is provided on the shaft 705 adjacent the tapered distal tip 701. A valve frame seat 718 is provided immediately proximal to the balloon 702, which is essentially a portion of the shaft 705. An ear hub 704 is provided on the shaft 705 immediately proximal to the valve frame seat 718. The ear hub 703 has one or more notches 720, where each notch 720 is adapted to be received by the opening in a corresponding eyelet 105. The remainder of the catheter can be embodied using principles and catheters that are well-known in the art, and will not be described as this is well-known to a person skilled in the art.

The capsule 703 has a hollow shaft with a lumen that is sized and configured to receive the shaft 705 of the balloon catheter. A blocking handle (not shown) is provided at the proximal end of the hollow shaft of the capsule 703 and functions to move the capsule 703 distally (to ensheath the prosthesis 80), and to withdraw the capsule 703 proximally (to release the prosthesis 80). The T-junction of the catheter can act as a block to limit the proximal travel of the blocking handle. The shaft 705 is received inside the lumen of the capsule 703, and the capsule 703 is adapted to cover the position of the balloon 702 and to be withdrawn proximally to completely expose the balloon 702 and the valve frame seat 718.

Figure 21:
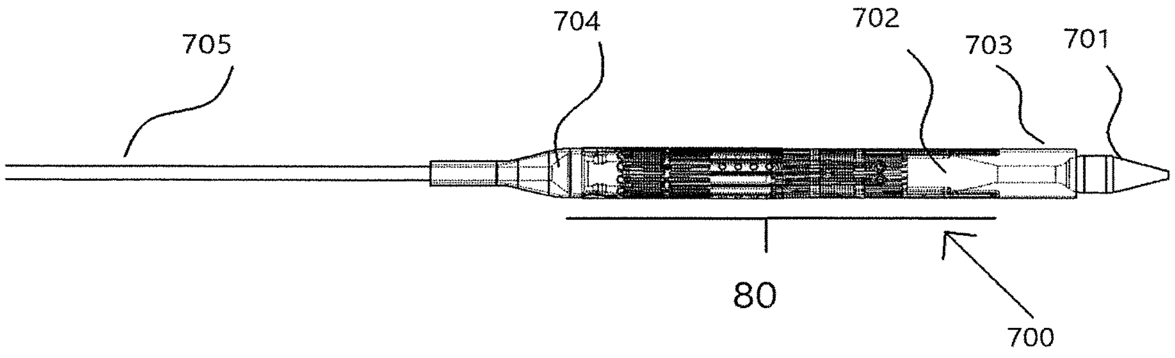
FIG. 21 is a schematic view of a delivery system according to the present invention showing the heart valve prosthesis of FIG. 1 compressed on the balloon.
Figure 22:
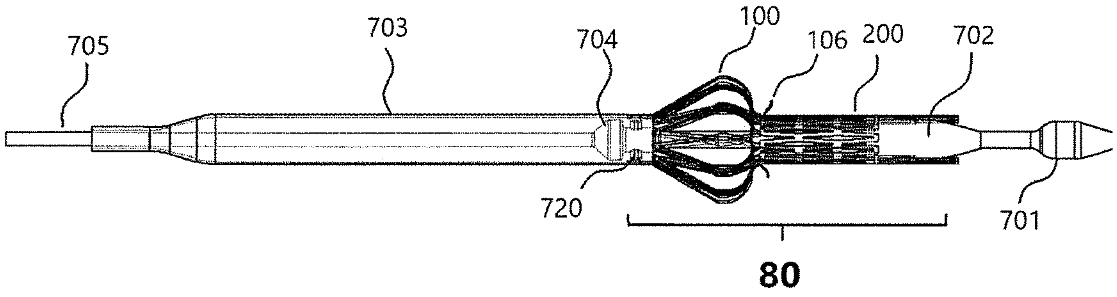
FIG. 22 is a schematic view of the delivery system of FIG. 21 showing the capsule partially withdrawn to allow the skirt dish to expand.
Figure 23:
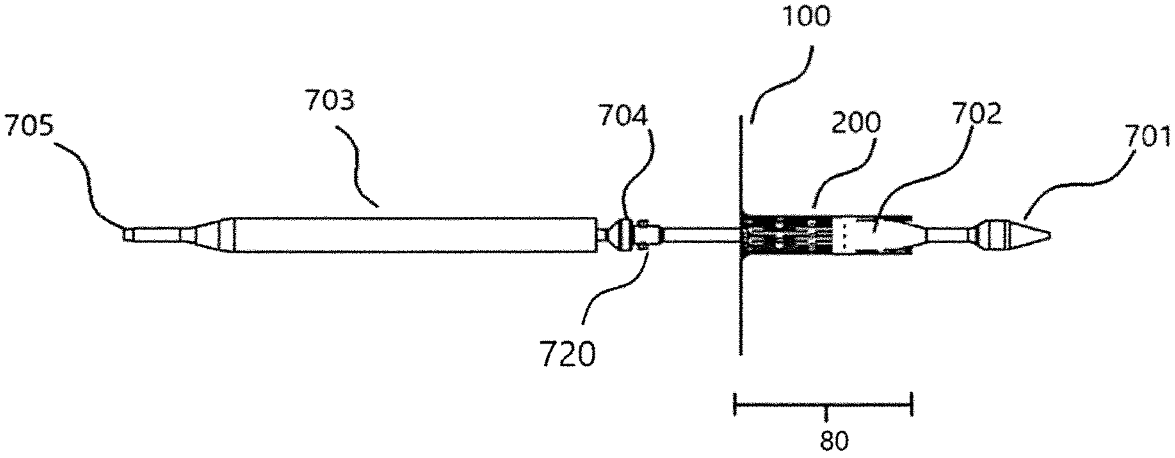
FIG. 23 is a schematic view of the delivery system of FIG. 21 showing the capsule completely withdrawn with the skirt dish completely expanded.
Figure 24:
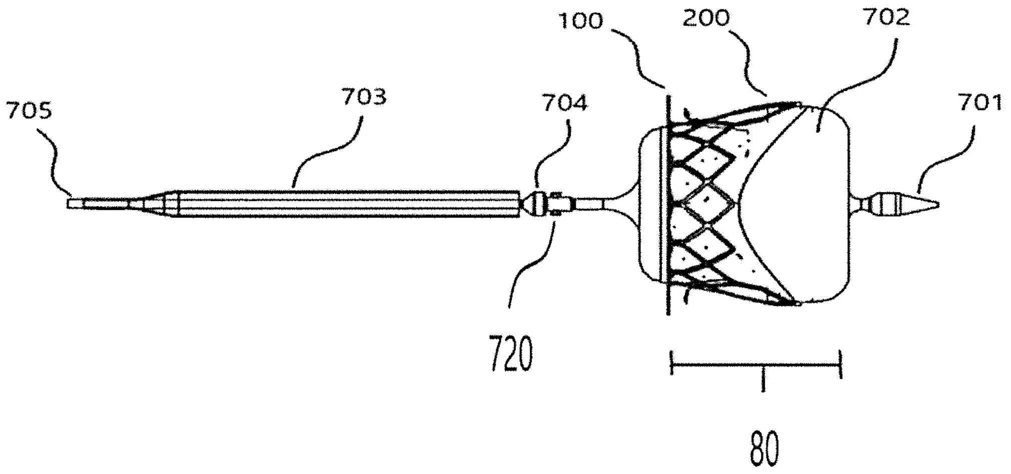
FIG. 24 is a schematic view of the delivery system of FIG. 21 showing the balloon fully expanded to deliver the valve support assembly.
Figure 25:
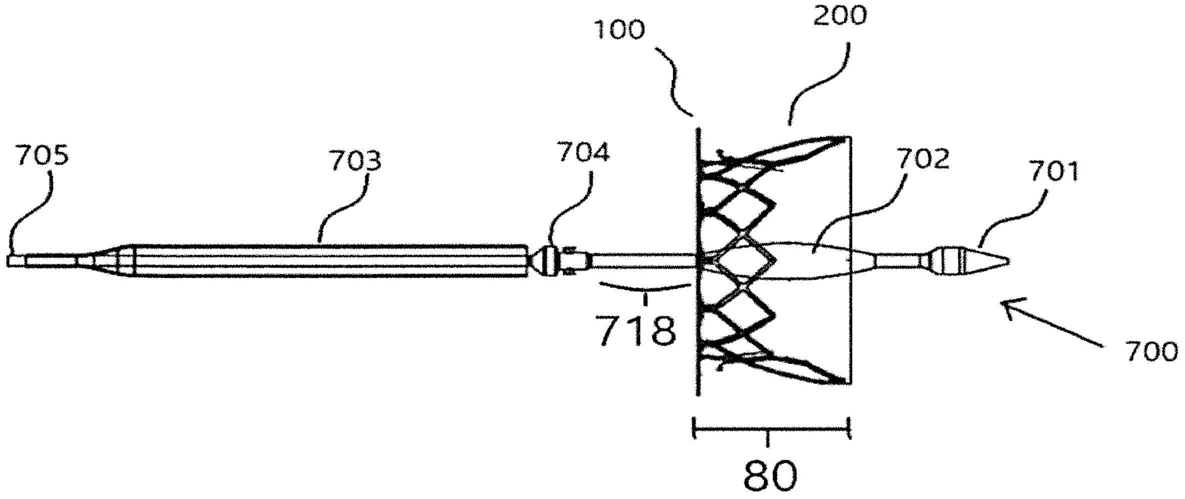
FIG. 25 is a schematic view of the delivery system of FIG. 21 showing the balloon deflated.
Figure 26:
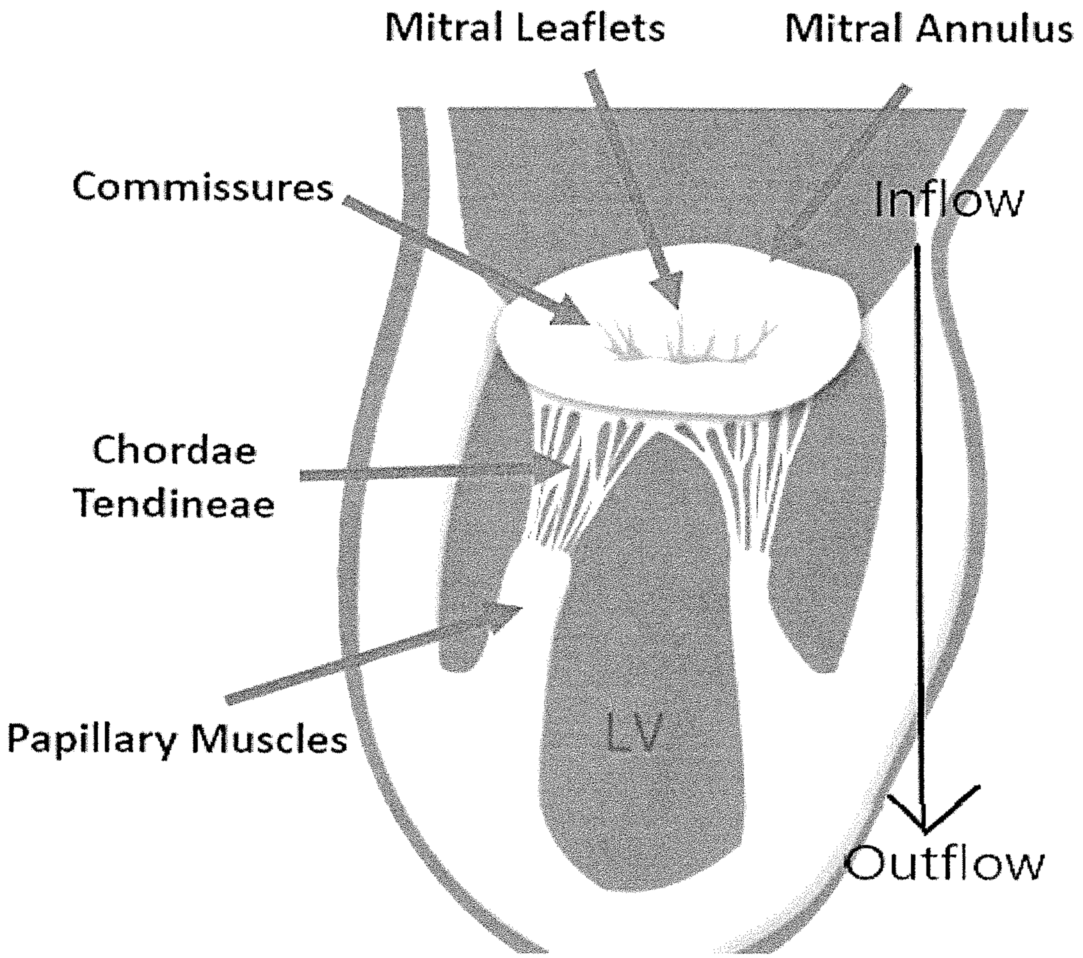
FIG. 26 illustrates a human mitral valve and its surrounding anatomy.

As shown in FIG. 21, the prosthesis 80 is positioned at the location of the balloon 702 and the valve frame seat 718. Specifically, the cobalt chromium valve support assembly 200 is crimped on to the balloon 702, and the skirt dish 100 is crimped on to the location of the valve frame seat 718. The capsule 703 is then advanced distally so that the capsule 703 completely covers both the skirt dish 100 and the valve support assembly 200.

When the prosthesis 80 has been delivered to the location of a native mitral annulus inside a patient, the capsule 703 can be withdrawn so that the distal end of the capsule 703 is at about the location of the ear hub 704 (see FIG. 22), and in this position, the skirt dish 100 begins to self-expand (see FIGS. 22 and 23) while the valve support assembly 200 remains crimped. Next, the balloon 702 is inflated (FIG. 24) to expand the valve support assembly 200. The capsule 703 is also further withdrawn (FIGS. 23 and 24) so that the capsule 703 releases the ear hub 704 and the eyelets 105 that are secured to the notches 720. Self-expansion of the eyelets 105 will cause the eyelets 105 to disengage from the notches 720. The balloon 702 is then deflated (FIG. 25) so that the balloon catheter can also be withdrawn.

Figure 27:
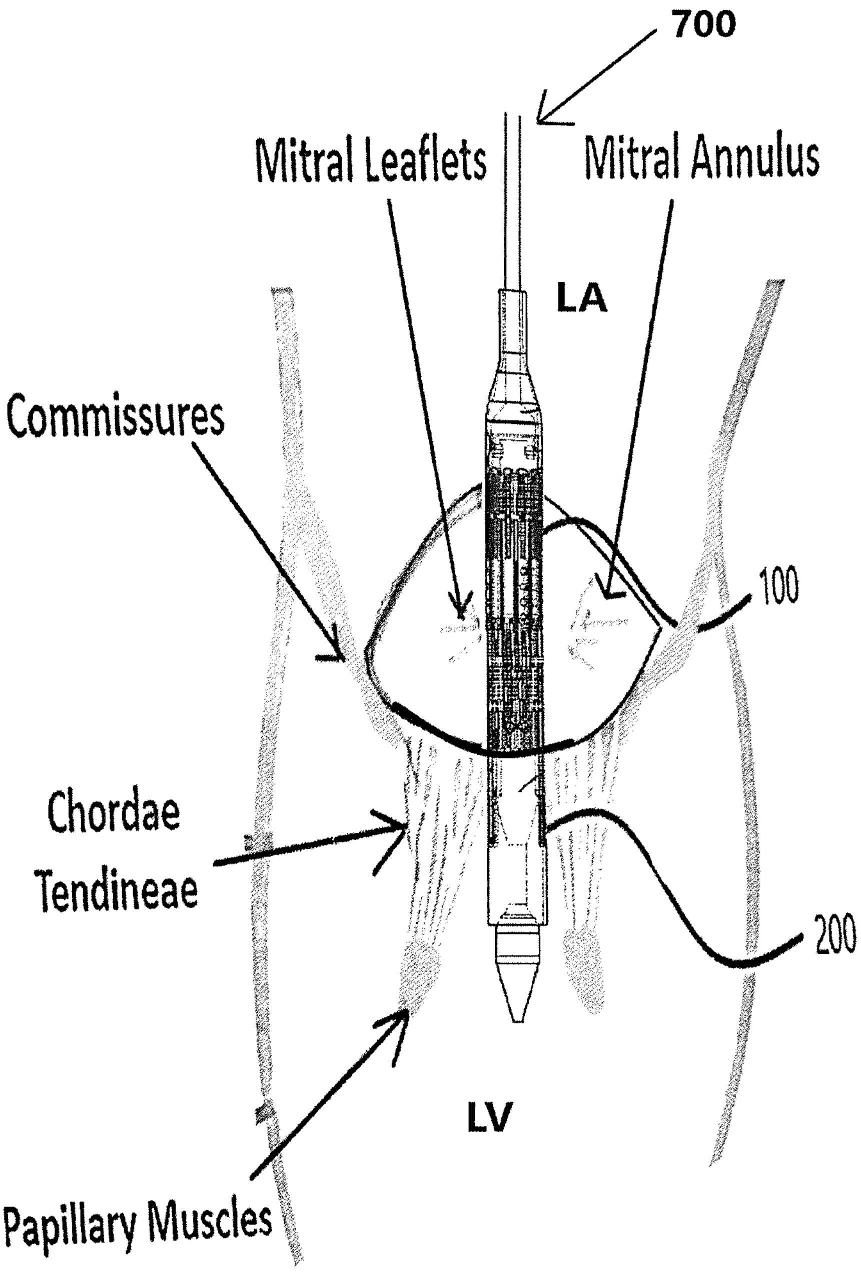
FIGS. 27-32 illustrate how the delivery system of FIG. 21 delivers and deploys the heart valve prosthesis of FIG. 1 at the mitral annulus of a human heart.
Figure 28:
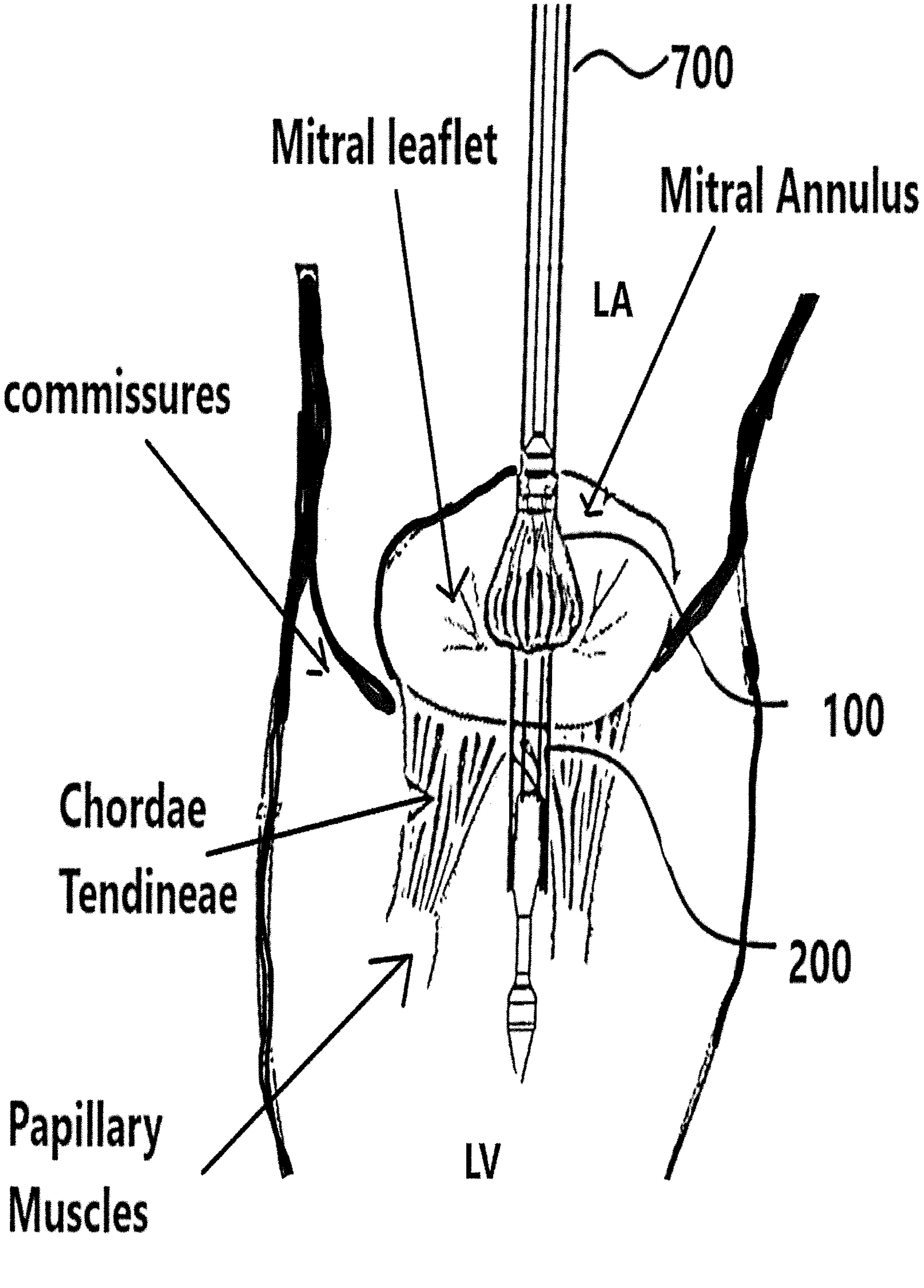
Figure 29:
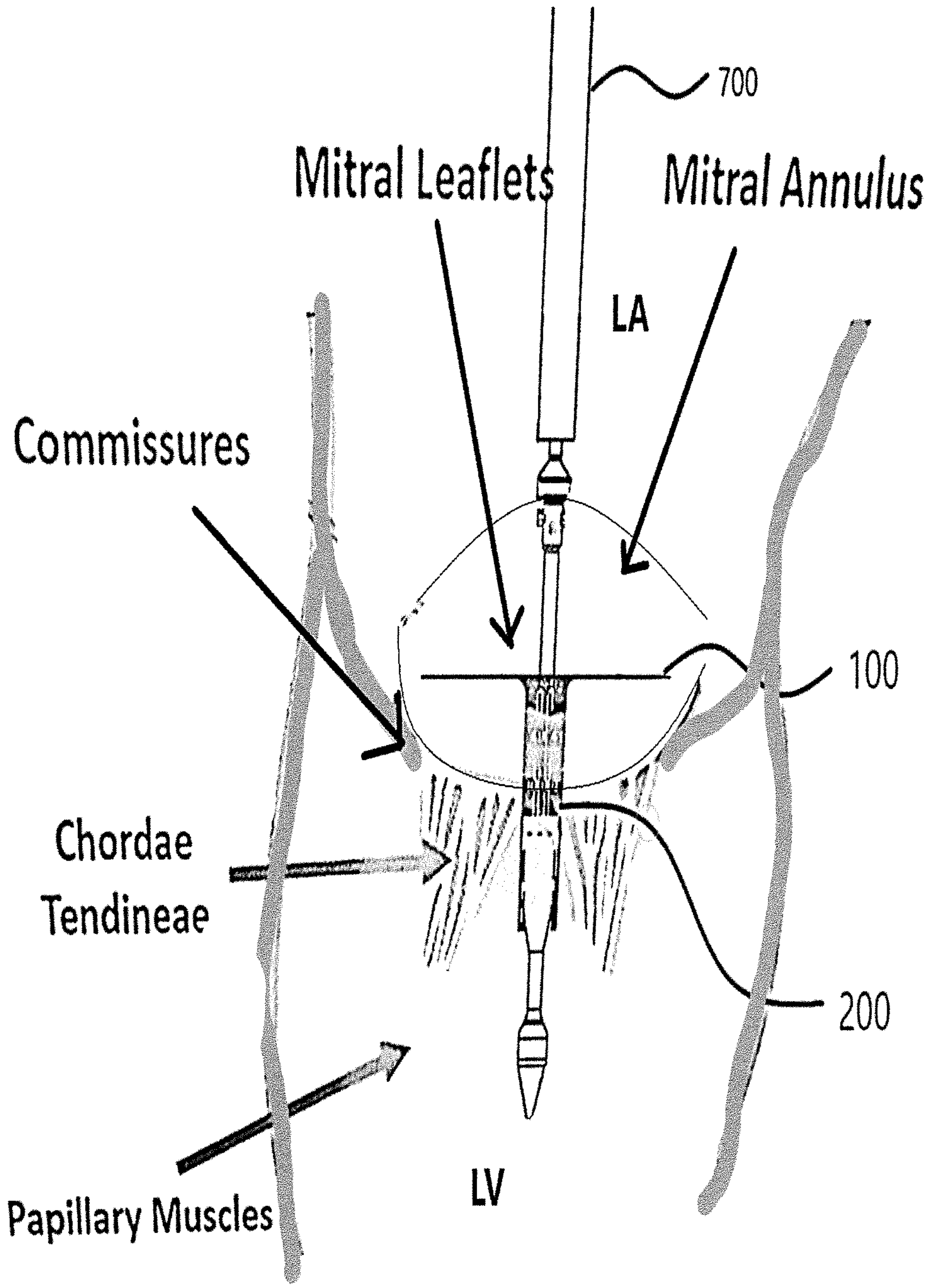
Figure 30:
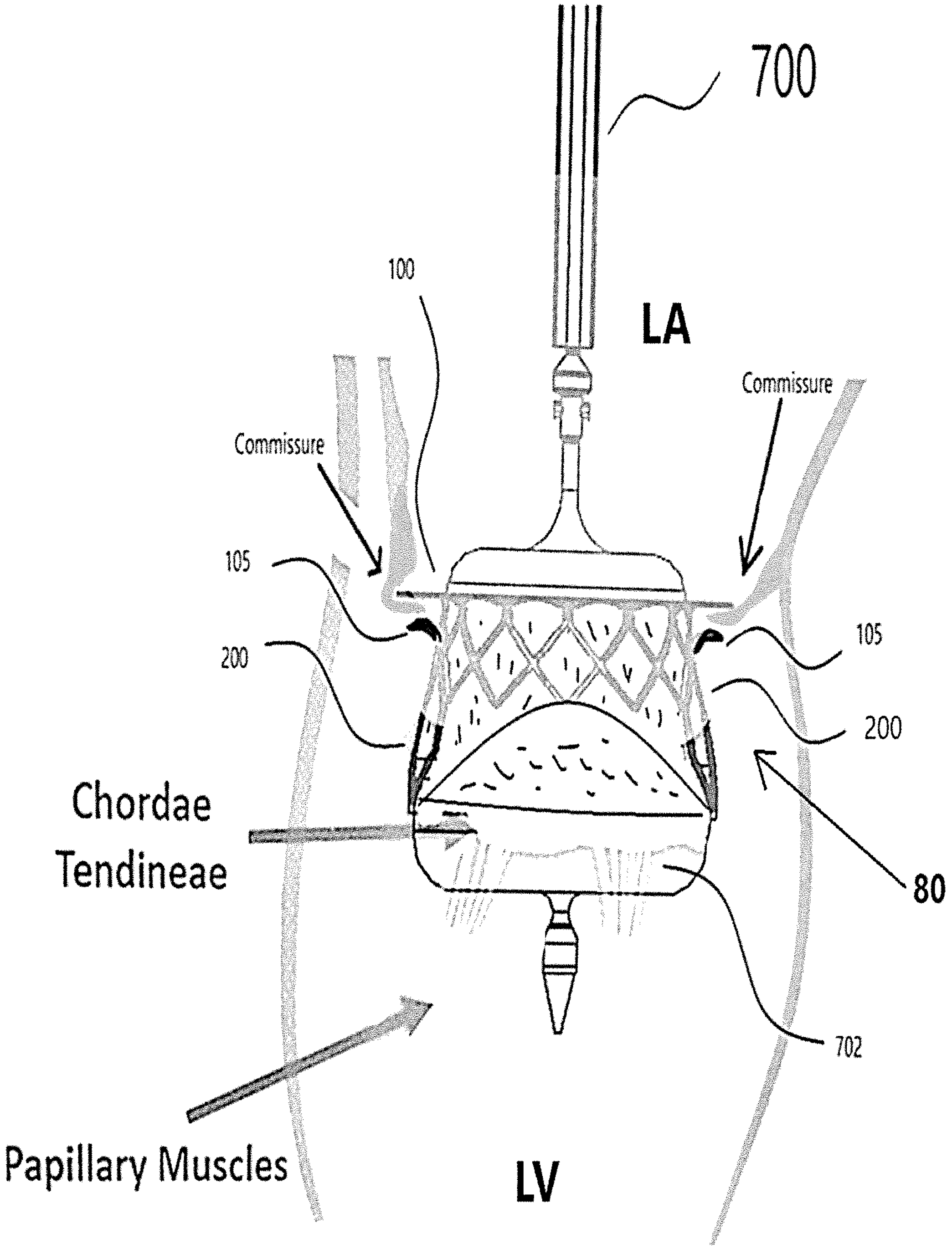

FIGS. 26-32 illustrate how the delivery system 700 delivers and deploys the prosthesis 80 at the mitral annulus of a human heart. Starting with FIG. 26, the delivery system 700 with the prosthesis 80 ensheathed by the capsule 703 is delivered from the left atrium through the left ventricle LV using transcatheter techniques that are well-known in the art. As shown in FIG. 27, the balloon catheter is preferably positioned so that the valve support assembly 200 is at the location of the mitral annulus. Next, the capsule 703 is withdrawn such that the distal end of the capsule 703 is at about the location of the ear hub 704 (see FIGS. 22-23 and 28-29). In this position, the skirt dish 100 begins to self-expand while the valve support assembly 200 remains crimped, and then the balloon 702 is inflated (see FIGS. 24 and 30) to expand the valve support assembly 200. The capsule 703 is then further withdrawn so that the capsule 703 releases the ear hub 704 and the eyelets 105 that are secured to the notches 720. The balloon 702 is then deflated (FIG. 31) so that the balloon catheter can also be withdrawn.

Figure 31:
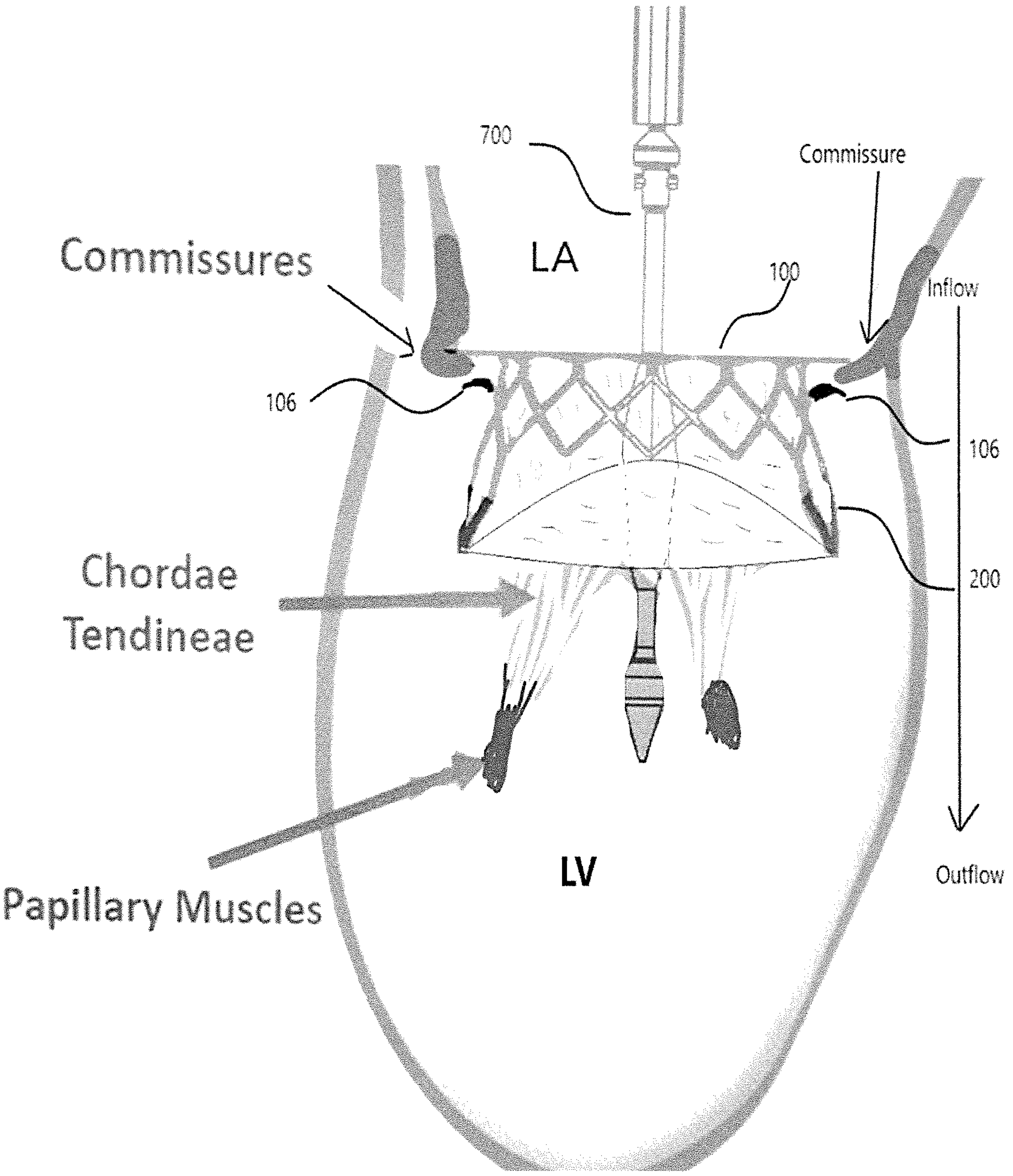
Figure 32:
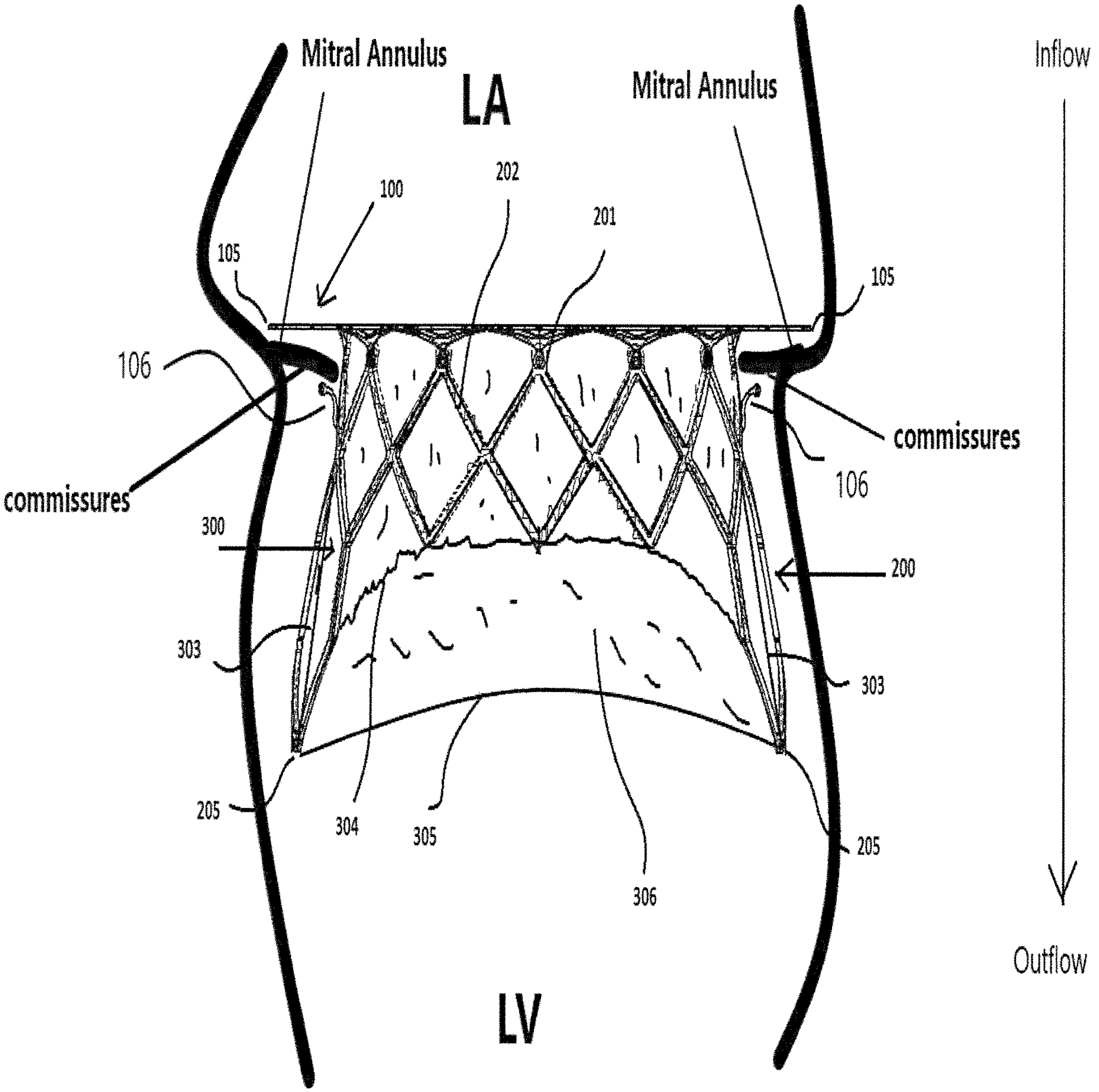

FIGS. 31 and 32 show the prosthesis 80 implanted at the mitral annulus. The skirt dish 100 sits on top of the mitral annulus so that the prosthesis 80 cannot move downstream. In addition, the anchors 106 are secured at the bottom of the commissures so that the prosthesis cannot move upstream. With the skirt dish 100 and the anchors 106 acting to "sandwich" or secure the prosthesis 80 at the mitral annulus, the prosthesis 80 provides an effective anchoring of the prosthesis 80 at the location of the mitral annulus.

The present invention provides a number of unique features and benefits.

First, the support skeleton 210 of the valve support assembly 200 is provided in a stronger and less flexible material, thereby providing more effective support for the prosthesis 80 at the mitral annulus. This is because when the valve leaflets close at the mitral position, the pressure is very high, so the stronger material effectively supports the commissures and prevent the outflow apices 205 from collapsing.

Second, since the frame assembly of the skirt dish 100 is made of Nitinol™ which is a more flexible material, the skirt dish 100 can more effectively surround the D-shaped mitral annulus to provide a better seal.

Third, both the skirt dish 100 and the valve support assembly 200 have a generally circular configuration when they are initially crimped, but assume a generally oval configuration when they are expanded for deployment, so as to provide a better fit for the D-shaped mitral annulus. This was an unexpected result in that the inventor did not realize that the skirt dish 100 and the valve support assembly 200 assume a generally oval configuration when they are expanded for deployment, until after experimentation revealed this characteristic. This feature is especially important because a cylindrical or circular configuration cannot effectively support a bileaflet assembly, which is better supported by a generally oval configuration.

Fourth, the prosthesis 80 allows the procedure to be very precise. Based on the two different materials for the Nitinol™ self-expanding skirt dish 100 and the cobalt chromium valve support assembly 200, when the prosthesis 80 is partially exposed by the capsule 703, the skirt dish 100 slowly self-expands while the valve support assembly 200 is still crimped on the balloon 702, thereby avoiding a "jump" or sudden expansion by the valve support assembly 200. This allows the physician time to position the prosthesis 80 and to inflate the balloon 702.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A mitral heart valve assembly, comprising:

a skirt dish having a tissue skirt sutured to the skirt dish, the skirt dish having a frame that is made of a plurality of cells, with each cell is made up of two straight sides connected at an apex, and with a concave side connected to the two straight sides, and wherein a connector extends vertically in an outflow direction from each concave side;

a valve support assembly having a leaflet assembly sutured to the valve support assembly, the leaflet assembly having a plurality of leaflets, the valve support assembly having a support skeleton that has a ring of valve support cells, with each valve support cell having an inflow apex which has an opening; and wherein the skirt dish is connected to the valve support assembly by positioning a portion of each connector inside a corresponding opening of a corresponding inflow apex in a manner such that the skirt dish defines a blood inflow side and the valve support assembly is downstream from the skirt dish, and wherein the skirt dish and valve support assembly are made from different materials.

2. The assembly of claim 1, wherein the skirt dish is made from a self-expanding material and the valve support assembly is made from a balloon expandable material.

3. The assembly of claim 1, wherein the valve support assembly is made from cobalt-chromium.

4. The assembly of claim 3, wherein the skirt dish is made from Nitinol.

5. The assembly of claim 1, wherein the skirt dish and the valve support assembly assume a circular configuration prior to crimping on to a delivery device, and assume an oval configuration after expansion.

6. The assembly of claim 1, wherein the leaflet assembly has two leaflets.

7. The assembly of claim 1, wherein the skirt dish has a frame assembly that has two hook-shaped anchors extending in the outflow direction.

8. A system, comprising:

a mitral heart valve assembly comprising:

a skirt dish having a tissue skirt sutured to the skirt dish, the skirt dish having a frame that is made of a plurality of cells, with each cell is made up of two straight sides connected at an apex, and with a concave side connected to the two straight sides, and wherein a connector extends vertically in an outflow direction from each concave side;

a valve support assembly having a leaflet assembly sutured to the valve support assembly, the leaflet assembly having a plurality of leaflets, the valve support assembly having a support skeleton that has a ring of valve support cells, with each valve support cell having an inflow apex which has an opening;

wherein the skirt dish is connected to the valve support assembly by positioning a portion of each connector inside a corresponding opening of a corresponding inflow apex; and wherein the skirt dish and valve support assembly are made from different materials;

a delivery system having:

a balloon catheter having a shaft having a distal end, a balloon provided on the shaft adjacent the distal end, and a valve frame seat located on the shaft directly proximal to the balloon;

a capsule provided on the shaft of the balloon catheter that slidably covers the balloon and the valve frame seat; and wherein the skirt dish is seated around the valve frame seat and the valve support assembly is seated over the balloon.

9. The system of claim 8, wherein:

an eyelet provided on the skirt dish;

an ear hub provided on the shaft immediately proximal to the valve frame seat; and the eyelet engages the ear hub when the skirt dish is seated around the valve frame seat and the valve support assembly is seated over the balloon.

10. The system of claim 8, wherein the skirt dish is made from a self-expanding material and the valve support assembly is made from a balloon expandable material.

11. The system of claim 8, wherein the valve support assembly is made from cobalt-chromium.

12. The system of claim 11, wherein the skirt dish is made from Nitinol.

13. The system of claim 8, wherein the skirt dish and the valve support assembly assume a circular configuration prior to crimping on to a delivery device, and assume an oval configuration after expansion.

14. A method of delivering a heart valve assembly to a mitral annulus which has native mitral leaflets, comprising:

providing a heart valve assembly comprising:

a skirt dish having a tissue skirt sutured to the skirt dish, the skirt dish having a frame that is made of a plurality of cells, with each cell is made up of two straight sides connected at an apex, and with a concave side connected to the two straight sides, and wherein a connector extends vertically in an outflow direction from each concave side;

a valve support assembly having a leaflet assembly sutured to the valve support assembly, the leaflet assembly having a plurality of leaflets, the valve support assembly having a support skeleton that has a ring of valve support cells, with each valve support cell having an inflow apex which has an opening;

the skirt dish is connected to the valve support assembly by positioning a portion of each connector inside a corresponding opening of a corresponding inflow apex; and wherein the skirt dish and valve support assembly are made from different materials;

providing a delivery system having:

a balloon catheter having a shaft having a distal end, a balloon provided on the shaft adjacent the distal end, and a valve frame seat located on the shaft directly proximal to the balloon;

a capsule provided about the shaft of the balloon catheter; and crimping the heart valve assembly on to the balloon catheter by seating the skirt dish around the valve frame seat and the valve support assembly over the balloon;

sliding the capsule to cover the balloon and the valve frame seat;

advancing the delivery system with the heart valve assembly ensheathed by the capsule to the location of a mitral annulus in a human heart;

withdrawing the capsule such that the capsule does not cover the skirt dish, such that the skirt dish begins to self-expand while the valve support assembly remains crimped;

inflating the balloon to expand the valve support assembly;

deflating the balloon; and withdrawing the balloon catheter.

* * * * *